US005593829A

United States Patent [19]
McCabe

[11] Patent Number: 5,593,829
[45] Date of Patent: Jan. 14, 1997

[54] METHOD FOR LABELING DNA BY RING-OPENING OF PURINE BASES

[75] Inventor: Mead M. McCabe, Miami, Fla.

[73] Assignee: University of Miami, Miami, Fla.

[21] Appl. No.: 241,385

[22] Filed: May 3, 1994

Related U.S. Application Data

[63] Continuation of Ser. No. 802,815, Dec. 6, 1991, abandoned.

[51] Int. Cl.$^6$ .................. C07H 21/04; C07H 19/167; C12Q 1/68; G01N 33/53
[52] U.S. Cl. .................. 435/6; 435/7.1; 435/975; 536/24.3; 536/25.32
[58] Field of Search .................. 536/23.1, 24.3, 536/24.31, 24.32, 25.32; 436/94; 435/6, 7.1, 975

[56] References Cited

U.S. PATENT DOCUMENTS

| | | | |
|---|---|---|---|
| 4,692,404 | 9/1987 | Ashihara et al. | 435/7.92 |
| 4,705,886 | 11/1987 | Levenson et al. | 560/159 |
| 4,849,505 | 7/1989 | Stavrianopoulos | 530/300 |

FOREIGN PATENT DOCUMENTS

WO84/93285  8/1984  WIPO.

OTHER PUBLICATIONS

Lebacq et al. (1988) *Journal of Biochemical and Biophysical Methods* 15: 255–266, "A New Sensitive Non–Isotopic Method Using Sulfonated Probes to Detect Picogram Quantities of Specific DNA Sequences on Blot Hybridization".
Sproat et al. (1989) *Nucleic Acids Research* 17: 3373–3387, Highly Efficient Chemical Synthesis of 2'-O-Methyloligoribonucleotides and Tetrabiotinylated Derivatives; "Novel Probes that are Resistant to Degradation by RNA or DNA Specific Nucleases".
Kochetkov et al. (1972) Organic Chemistry of Nucleic Acids: Chapter 7, pp. 382–423, "Reactions Involving Cleavage or Rearrangement".
Takahashi et al. (1989) *Nucleic Acids Research* 17: 4899–4900, "A New Biotinylating System for DNA Using Biotin Aminocaproyl Hydrazide and Glutaraldehyde".
Pochon et al. (1967) *Biochim. Biophys. Acta* 149: 99–106, "Polynucleotides IX. Methylation of Nucleic Acids, Homopolynucleotides and Complexes".
Mattes et al. (1986) *Biochimica et Biophysica Acta* 868: 71–76, "Mechanism of DNA Strand Breakage by Piperidine at Sites of N7–alkylguanines".
Langer et al. (1981) *Proc. Natl. Acad. Sci. USA* 78: 6633–6637, "Enzymatic Synthesis of Biotin–labeled Polynucleotides: Novel Nucleic Acid Affinity Probes".
Leary et al. (1983) *Proc. Natl. Acad. Sci. USA* 80: 4045–4049, "Rapid and Sensitive Colorimetric Method for Visualizing Biotin–labeled DNA Probes Hybridized to DNA or RNA Immobilized on Nitrocellulose: Bio–blots".
Gebeyehu et al. (1987) *Nucleic Acids Research* 15: 4513–4535, "Novel Biotinylated Nucleotide—Analogs for Labeling and Colorimetric Detection of DNA".
Gardner (1983) *BioTechniques* 2: 38–42, "Non–radioactive DNA Labeling: Detection of Specific DNA and RNA Sequences on Nitrocellulose and in situ Hybridizations".
Reisfeld et al. (1987) *Biochemical and Biophysical Research Communications* 142: 519–526, "Nonradioactive Hybridization Probes Prepared by the Reaction of Biotin Hydrazide with DNA".
Gillam et al. (1986) *Analytical Biochemistry* 157: 199–207, "$N^4$–(6–Aminohexyl)cytidine and –deoxycytidine Nucleotides Can Be Used to Label DNA".
Verdlov et al. (1974) *Biochimica et Biophysica Acta* 340: 153–165, "Modification of Cytidine Residues With a Bisulfite–O–methylhydroxylamine Mixture".

*Primary Examiner*—Gary L. Kunz
*Attorney, Agent, or Firm*—Foley & Lardner

[57] ABSTRACT

The invention provides methods for attaching detectable labels to the $N^7$-formyl group, of imidazole ring-opened alkylated purines and purine derivatives, directly, through a linking group, or by subsequent derivatization of a blocking group. The invention provides simple and efficient methods for labeling polynucleotides. In addition, the invention provides derivatized ring-opened alkylated purines and purine derivatives, including reagents for chemical and enzymatic synthesis of detectably labeled polynucleotides.

19 Claims, 7 Drawing Sheets

FIG. 1

FORMATION OF N⁷-FORMYL-N⁷-METHYL DEOXYGUANOSINE

FIG. 2

LABELING BY FORMATION OF SCHIFF BASES OR HYDRAZONES

R-CHO = $N^7$-FORMYL-$N^7$-METHYL DEOXYGUANOSINE
R' = DETECTABLE LABEL

FIG. 3

BIOTINYLATION BY FORMATION OF SCHIFF BASES OR HYDRAZONES

R-CHO = $N^7$-FORMYL-$N^7$-METHYL DEOXYGUANOSINE
R' = AMINOCAPROYL BIOTIN

METHOD FOR LABELING DNA BY RING-OPENING OF PURINE BASES

The invention described herein was developed, in part, using funds provided by the National Institutes of Health, Department of Health and Human Services, Grant No. 2-R01 DE 04321.

This application is a continuation of application Ser. No. 07/802,815, filed Dec. 6, 1991, now abandoned.

The present invention relates to methods for labeling nucleosides and polynucleotides by purine ring-opening reactions, to labeled nucleosides and polynucleotides obtained by the ring-opening reactions, and to the use of the labeling reactions and labeled products to detect polynucleotides in a sample.

BACKGROUND OF THE INVENTION

The detection of polynucleotides is important in many areas of molecular biology, biochemistry, biology, pharmacology and clinical medicine, inter alia. Sometimes it is important to detect the presence per se of any polynucleotide in a sample, as is the case particularly for producing protein-based therapeutic agents intended for human use, for instance. Other times it is desired to detect a specific polynucleotide sequence present in a multitude of sequences. For instance, the diagnosis of genetic disorders depends on sequence-specific polynucleotide detection and sequence-specific nucleic acid hybridization probes play a central role in molecular biology research where they are used for the detection of specific, complementary nucleic acid sequences present in minute amounts in a background of large quantities of other polynucleotides. Assays involving nucleic acid hybridization in the future will be ubiquitous in the clinical lab, and will find widespread application in other areas, including, for instance, veterinary medicine, forensic medicine, plant breeding and other areas of agriculture.

Whether it is desired to detect the presence, per se, of polynucleotides in sample, or to detect a particular polynucleotide sequence, a key step is labeling the polynucleotide or polynucleotide probe with a detectable label. Generally, the specificity and sensitivity of a detection method will be at least partly determined by the properties of the detectable label and the efficiency of the labeling method used to introduce the label into the polynucleotide.

Various labeling techniques have been developed that provide the selectivity and efficiency necessary to detect DNA present at fairly low levels in a sample, and to label hybridization probes sufficiently to detect specific sequences of DNA present in a high background of other sequences. For instance, radioisotopes such as $^3H$, $^{14}C$, $^{32}P$, $^{35}S$ and $^{125}I$ have been incorporated into polynucleotides by metabolic, enzymatic and chemical means to serve as detectable reporter groups to indicate the presence of polynucleotides in a sample $^{32}P$ and $^{35}S$, have proven particularly useful in molecular biology studies in such techniques as RNA and DNA sequencing, and the panoply of blot-hybridization methods used to detect, identify, measure, quantitate and localize specific polynucleotide sequences.

Radioactive labels suffer from several drawbacks, however. First, there is the risk of human exposure to hazardous levels of radioactivity during the preparation, use and disposal of reagents containing a radioactive tag. In consequence of the risk associated with human exposure to radiation there is a need when working with radiation for elaborate and expensive safety precautions.

In addition, the radioisotopes most suitable for use in nucleic acid research have relatively short half-lives. For instance, $^{32}P$ has a half-life of only 14 days, and $^{35}S$ has a half-life of only 87 days. Radioactively labeled probes therefore have limited shelf-lives and cannot be prepared and standardized in large batches, well before actual use. The necessity to prepare probes in small batches close to the time of actual use incurs economic disadvantages of scale. Furthermore, the inability to prepare and characterize large batches of radioactively labeled probes is a barrier to developing polynucleotide based diagnostic reagents.

The disadvantages of radioactive labels has led to the development of alternative techniques for introducing stable non-radioactive, detectable labels into polynucleotides. Thus, methods have been developed to label polynucleotides with, inter alia, biotin, digoxigenin and sulfonate.

Perhaps the most widely used non-radioactive polynucleotide label is biotin. Biotin binds with exceptional specificity and avidity to the proteins avidin and streptavidin. Thus, these proteins will bind with exceptional efficiency to biotinylated DNA. Both proteins can be cross-linked to an enzyme to form an enzymatically active conjugate, in which the avidin or streptavidin portion specifically detects the biotin in biotinylated DNA and the enzymatic portion catalyses the formation of a detectable product, such as a colored or luminescent product, which can be determined quantitatively and indicates the presence and the amount of biotinylated DNA in the sample. Avidin-alkaline phosphatase conjugates which are compatible with standard EIA colorimetric reagents have been widely employed in this type of biotin-based procedure.

Other labels, such as digoxigenin, can be used in analogous fashion. Thus, digoxigenin may be incorporated into the DNA analogously to biotin and the digoxigenin-DNA adduct detected by ELISA or other EIA techniques using an enzyme conjugated to an anti-digoxigenin polyclonal or monoclonal antibody.

In view of the widespread utility of labeled polynucleotides, simple, efficient and reliable methods for labeling polynucleotides are needed. The methods presently available, however, suffer from a number of disadvantages. For instance, biotinylated polynucleotides are produced using biotinylated nucleoside derivatives which must be chemically synthesized and then incorporated into a polynucleotide by enzymatic or chemical reactions. Thus, substrates for the preparation of biotinylated and digoxigeninylated polynucleotides are analogues of the native nucleoside and deoxynucleoside triphosphates, with chemical groups covalently coupled to the base. Examples of such analogues are uridine and deoxyuridine triphosphate (UTP and dUTP) coupled via a spacer arm to biotin (biotin-11-dUTP and biotin-11-UTP), or to digoxigenin (digoxigenin-11-dUTP and digoxigenin-11-UTP), in which the detectable group is attached at C5 of the uridine base. See Langer et al., *Proc. Nat'l. Acad. Sci., U.S.A.* 78: 6633–6637 (1981) and Brigati et al., *Virology* 126: 36–50 (1983).

Methods for synthesizing biotinylated or digoxigeninylated precursors, however, are time-consuming and require considerable expertise in synthetic chemistry. Moreover, labeling polynucleotides with these substrates generally requires expensive enzymes and exacting reaction conditions. Thus, such substrates cannot be used in many situations and are not suitable for the synthesis of large amounts of labeled polynucleotide.

Photoreactive derivatives of biotin and digoxigenin, such as those described by Forster et al., *Nucl. Acids Res.* 13: 745

(1985), provide a non-enzymatic means of incorporating biotin or digoxigenin into polynucleotides, including double-stranded DNA (dsDNA), single-stranded DNA (ssDNA) and RNA. The photoreactive derivatives must be chemically synthesized, however, a technically demanding and expensive process. In addition, the polynucleotides being labeled must be pure since the photochemical reactions are not specific and contaminating compounds such as proteins are readily labeled. The density of labeling is low with this procedure, being on the order of one label per 200 base residues. Furthermore, polynucleotides labeled using the photoreactive derivatives often bear biotin or digoxigenin on sites involved in Watson-Crick hydrogen bonding, which can deleteriously affect the ability of a probe to bind to its target sequence in a sample.

Several chemical procedures for incorporating detectable groups into polynucleotides have been described. For instance, Stavrianopoulos in U.S. Pat. No. 4,843,122 described a method for biotinylating DNA wherein guanine C8 is activated with 3,4,5-trichloroaniline and then bonded to biotin-SH. Reisfeld et al., *Biochem. Biophys. Res. Comm.* 142: 519 (1987), described the bisulfite catalyzed bonding of biotin hydrazide to cytidine $N^4$ in DNA. Takahashi et al., *Nucleic Acids Res.* 17: 4899 (1989), described the coupling of biotin aminocaproylhydrazide to single-stranded DNA by reaction with glutaraldehyde, possibly resulting in substitution at $N^6$ of adenosine, $N^2$ of guanosine and $N^4$ of cytosine. Sverdlov et al., *Biochim. Biophys. Acta.* 340: 153 (1974), described the sulfonation of cytosine C6, accompanied by substitution of the exocyclic $N^4$ amino group with methoxyamine, forming $N^4$-methoxy-5,6-dihydro-cytosine-6-sulfonate.

Biotin ligands in polynucleotides labeled according to these procedures serve as biotin receptor (e.g., avidin and streptavidin) binding sites, allowing detection of biotinylated DNA by ELISA and other EIA methods, inter alia, as described above. Similarly, polynucleotides labeled by $N^4$-methoxy-5,6-dihydro-cytosine-6-sulfonate bind a monoclonal antibody against $N^4$-methoxy-5,6-dihydro-cytosine-6-sulfonate and are detected in much the same way as biotin by ELISA and other EIA methods.

All of these methods suffer from a variety of disadvantages. Some methods require cumbersome procedures. Some methods can introduce only a single molecule of detectable label into each polynucleotide molecule. None of the methods can be used to label polynucleotides in a complex mixture of many different contaminants.

Methods have also been described for incorporating a label into a polynucleotide made by chemical synthesis techniques. For instance, Ruth, *DNA* 3: 123 (1984), described a method for incorporating detectable labels into purified polynucleotides of defined sequence by chemical synthesis. Ruth described nucleosides bearing functionalized linkers suitable for use in oligonucleotide synthesizers. Synthetic single-stranded oligonucleotides of defined sequence were produced bearing the functionalized linkers on pre-selected bases in the sequence. The functional group could be a detectable label or could be joined to a detectable label following synthesis. Production of the derivatized nucleosides of Ruth's method requires considerable technical skill, however, and their utility is limited to labeling synthetic oligonucleotides.

Jablonski et al., *Nucleic Acids Res.* 14: 6115 (1986), showed that the homobifunctional reagent disuccinimidyl suberate can be used to directly cross-link an oligonucleotide with the enzyme alkaline phosphatase, through a single amine-modified base in the oligonucleotide. This method, however, is limited to oligonucleotides containing the amine-modified base. Furthermore, the alkaline phosphatase may interfere with base pairing by the oligonucleotide in a hybridization assay.

In sum, despite the importance of labeled polynucleotides in molecular biology, biochemistry and clinical diagnostic applications, inter alia, a simple, reliable, efficient and widely applicable procedure for introducing detectable labels into polynucleotides has not been developed. All of the procedures discussed hereinabove are of limited applicability. Few methods provide for introducing many labels into each polynucleotide. Conventional enzymatic labeling methods require expensive enzymes, highly purified nucleic acid templates and substrates, and reaction conditions must be stringently controlled. Furthermore, the efficiency of labeling by these methods is difficult to determine, making it hard to assess usefulness of a labeled product before use.

Photochemical and chemical (sulfonation) procedures have a wider range of applicability but require cumbersome chemical procedures and also require purified nucleic acid substrates. Although many of the prior art procedures can be completed within a few hours, they may require extensive preliminary preparations and the entire process is usually very time consuming. Furthermore, excepting photochemical labeling and the automated synthesis of labeled oligonucleotides, labeling procedures yield very small amounts (microgram quantities) of labeled product.

SUMMARY OF THE INVENTION

It is therefore an object of the present invention to provide a method for labeling polynucleotides which is simple, reliable, efficient and sensitive, and can be applied to labeling pure polynucleotides or polynucleotides in the presence of contaminants.

It is a further aspect of the invention to provide a simple and efficient method to label polynucleotides for use as probes in hybridization assays, inter alia.

Yet another object of the present invention is to provide a simple, efficient and highly sensitive method to quantitatively detect polynucleotides in a sample.

It is also an object of the present invention to provide a means for introducing a detectable label into a nucleoside derivative suitable for labeling a polynucleotide via chemical synthesis or enzymatic-labeling techniques.

It is a further object of the present invention to provide nucleoside derivatives which comprise detectable labels or functional groups suitable for bonding to detectable labels.

It is yet another object of the present invention to provide polynucleotides which comprise detectable labels or functional groups suitable for bonding to detectable labels.

The invention thus provides a variety of means to derivatize nucleosidic compounds, including nucleosides, nucleoside derivatives, oligonucleotides and polynucleotides, to introduce therein by means of a purine ring-opening reaction, a reactive moiety suitable for attaching thereto a protecting or blocking group, a linking group, or another intermediate group, and, ultimately a substituent comprising a detectable label.

In another aspect, the invention provides novel compounds, including but not limited to ring-opened substituted purine derivatives, and oligo and polynucleotides comprising the ring-opened substituted purine derivatives. Thus, for instance, the invention provides ring-opened purine derivatives suitable for use as precursors in synthetic oligonucleotide synthesizers. And, as another example, the invention provides derivatized polynucleotides, either detectably labeled, or derivatized so as to facilitate the introduction of a detectable label, which are suitable for use, inter alia, as hybridization probes.

The invention also provides reagents, procedures and kits for labeling polynucleotides by means of ring-opened purine derivatives, to detect, identify, measure, quantitate or localize polynucleotides in a sample, in either a sequence-specific or a sequence independent manner, or both.

Thus, the invention relates to methods for labeling nucleosides and polynucleotides by means of purine ring-opening reactions to produce a formyl group which group is then further derivatized to comprise, ultimately, a detectable label, to the products produced by the methods, and to the uses of the methods and the products in detecting polynucleotides.

In accomplishing the foregoing objects, there has been provided, in accordance with another aspect of the present invention a method for labeling a polynucleotide comprising at least one purine nucleotide, comprising the steps of (a) alkylating a purine ring nitrogen in a nucleotide in a polynucleotide to form an N-alkylated purine nucleotide; (b) cleaving a bond in the N-alkylated purine nucleotide to form a ring-opened N-alkyl-N-formyl nucleotide; and, (c) chemically bonding a detectable label to the N-formyl group, either directly or through a linking group.

In a preferred embodiment of this aspect of the invention there has been provided a method for labeling a polynucleotide that comprises at least one guanine nucleotide, comprising the steps of (a) $N^7$-alkylating a guanine nucleotide in the polynucleotide to form an $N^7$-alkylguanine nucleotide; (b) cleaving the $C8$-$N^9$ bond in the $N^7$-alkylguanine nucleotide to form a ring-opened $N^7$-formyl-$N^7$-alkylguanine nucleotide; and, (c) chemically bonding a detectable label to the $N^7$-formyl group, either directly or through a linking group.

In a particularly preferred embodiment of the invention there is provided a method for labeling polynucleotides comprising at least one guanine nucleotide comprising steps of (a) mixing dimethylsulfate (DMS) in a neutral buffer with the polynucleotide; (b) incubating the DMS and polynucleotide-containing solution under conditions suitable for $N^7$-methylation of the guanine nucleotide in the polynucleotide to form an $N^7$-methylguanine nucleotide; (c) adding a base to the solution of step (b) in an amount sufficient to cleave the bond between C8 and $N^9$ in the $N^7$-methyl guanine nucleotide to form a ring-opened $N^7$-formyl-$N^7$-methylguanine nucleotide in a polynucleotide in the sample; and, chemically bonding a detectable label to the $N^7$-formyl group of the $N^7$-formyl-$N^7$-methylguanine nucleotide, either directly or through a linking group.

In another aspect of the invention, using the foregoing methods, there has been provided a method for detecting a polynucleotide comprising at least one purine nucleotide in a sample, comprising the step of detecting the polynucleotide in the sample by determining a detectable label chemically bonded to an N-formyl group formed in the purine nucleotide.

In accordance with another aspect of the invention there have been provided compounds according to the following formula:

wherein, A is —H or —OH; B is —H, —OH, mono-, di- or triphosphate or a derivative thereof, or a protecting group for chemical polynucleotide synthesis; D is —H, —OH, mono-, di- or triphosphate or a derivative thereof, or a protecting group for chemical polynucleotide synthesis; E is an alkyl group; F is a bond or linking moiety; and, G is a detectable label or a blocking group.

In accordance with another aspect of the invention there have been provided polynucleotides comprising a compound according to the following formula:

wherein: A is —H or —OH; B is —H, —OH, or mono-, di- or triphosphate or a derivative thereof, or a phosphodiester bond or a derivative thereof; D is —H, —OH or mono-, di- or triphosphate or a derivative thereof, or a phosphodiester bond or a derivative thereof; E is an alkyl group; F is a bond or linking moiety, and; G is a detectable label.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those in the art from this detailed description.

GLOSSARY

The term $N^7$-formyl-$N^7$-alkylpurine is used herein to designate certain ring-opened compounds of the invention which may also be called alkylformamidopyrimidine or 2,4,5-triamino-6-hydroxy-$N^5$-methyl-$N^5$-formylpyrimidine compounds, inter alia, but herein are referred to as $N^7$-formyl-$N^7$-alkylpurine or ring-opened $N^7$-formyl-$N^7$-alkylpurine, and, in the case of guanine and guanosine, $N^7$-formyl-$N^7$-alkylguanine and $N^7$-formyl-$N^7$-alkylguanosine, or ring-opened $N^7$-formyl-$N^7$-alkylguanine and ring-opened $N^7$-formyl-$N^7$-alkylguanosine. Another name for these alkylguanine deoxynucleoside derivatives is 2-amino-5-(formyl-alkylamino)-6-(2'-deoxyribosylamino)-pyrimidin-4-one, which for $N^7$-formyl-$N^7$-methylguanosine is 2-amino-5-(formyl-methylamino)-6-(2'-deoxyribosylamino)-pyrimidin-4-one.

DETAILED DESCRIPTION OF THE INVENTION

The present invention overcomes many of the problems of labeling polynucleotides found in the prior art. Particularly, in some aspects, it eliminates the need for complex chemical or enzymatic reactions. It does not require the use of highly pure nucleic acids and is universally applicable to any polynucleotide containing one or more purine, preferably guanine residues. Moreover, because the label targets portions of a probe molecule which are not involved with hydrogen bonding to the target nucleic acid, probes labeled according to the method of the invention are likely to be unimpaired in the recognition and binding of target nucleic acids. This feature allows higher density of labeling, thus enhancing the sensitivity of the invention, and the simplicity of the reaction and lack of a requirement for enzymes renders the method of the present invention less prone to error.

Accordingly, the present invention relates to methods for labeling and detecting polynucleotides by means of a purine ring-opening reaction. More specifically, the present invention relates to an alkylation and ring-opening reaction that cleaves the imidazole ring of a purine and introduces a formyl group into the opened imidazole ring, and, in particular, to the derivatization of the formyl group to introduce detectable substituents into the ring-opened purine derivatives.

In accordance with the invention the ring-opening and derivatization reaction may be carried out on a purine nucleoside or a polynucleotide containing a purine nucleotide, particularly guanine nucleoside and nucleoside derivatives and guanine nucleotide-containing polynucleotides, including ribo- and deoxyribopolynucleotides, which may be single stranded, double stranded, or triple stranded polynucleotides, inter alia.

In one aspect the invention provides for detecting, identifying, measuring, quantitating, or localizing, inter alia, polynucleotides in a biological sample. This aspect of the invention is equally useful to detect polynucleotides in a sequence-independent manner and to detect specific polynucleotide sequences.

Thus, the invention provides a highly sensitive method to detect, in a sequence-independent manner any RNA or DNA in a biological sample, such as a protein preparation or any other composition prepared from or exposed to a biological source of RNA or DNA, or in which such RNA or DNA might desirably be detected.

Notably, this aspect of the invention provides for the introduction into each polynucleotide in a sample of a multiplicity of detectable labels by the derivatization of multiple purine, preferably guanine, nucleotides in each polynucleotide. The introduction of multiple detectable moieties into each polynucleotide molecule provides an extremely sensitive means of detecting such polynucleotides.

The invention also provides means for labeling polynucleotides which may be used for sequence-dependent detection, identification, measurement, quantitation or localization of polynucleotides. For instance, this aspect of the invention provides for labeling a polynucleotide for use as a hybridization probe. In general, individual RNA and DNA sequences are most useful for this purpose, but any polynucleotide preparation capable of identifying by base-pairing a polynucleotide of interest can be employed as a hybridization probe.

Thus, the invention may be employed to label any polynucleotide as a hybridization probe, including, for instance, synthetic oligonucleotides, restriction fragments, plasmids, cosmids, phage, etc., individual RNAs or DNAs, crude preparations of RNA or DNA, including transfer RNA (tRNA), ribosomal RNA (rRNA), messenger RNA (mRNA) or mitochondrial, epigenomic or genomic DNA, or fragments thereof or mixtures thereof.

In general, polynucleotides to be used as hybridization probes (or, indeed, for other purposes) in accordance with the invention may be labeled by chemical synthesis by incorporating a residue previously derivatized in accordance with the invention; by enzymatic means, such as nick translation, "fill-in", transcription, reverse transcription, and the like, to incorporate a residue previously derivatized according to the invention into a polynucleotide; and by derivatizing, in accordance with the invention, a nucleotide within or at one or the other end of a polynucleotide. A variety of such reactions are known, as described, for instance, in Maniatis, et al., MOLECULAR CLONING, A LABORATORY MANUAL (Cold Spring Harbor Laboratory, 1982) and Sambrook, et al., MOLECULAR CLONING, A LABORATORY MANUAL, Second Edition, Vol. 1–3 (Cold Spring Harbor Laboratory, 1989).

The invention combines a series of reliable reactions into a new technique for specifically coupling a detectable label to purine, preferably guanine residues in nucleosides, nucleoside derivatives, polynucleotides and polynucleotide derivatives, inter alia.

The initial reaction involves the selective alkylation of a purine ring nitrogen by an alkylating agent. In a preferred embodiment, guanine $N^7$ is alkylated, selectively. Suitable alkylating agents of the invention include but are not limited to dimethylsulfate (DMS) and diethylsulfate, for instance.

In a highly preferred embodiment of the invention, alkylation is carried out using DMS. When DMS is used in the invention to alkylate, DNA, the reaction is preferably carried out at neutral pH. This reaction is similar to the first step of the guanosine-specific cleavage in the Maxam-Gilbert sequencing technique, which is described in Maxam et al., *Methods in Enzymology* 65: 449 (1980), inter alia.

The degree of methylation obtained by this reaction can be controlled by varying the incubation time, the concentration of DMS, and the temperature of the reaction, among others. The degree of alkylation determines the number of imidazole ring-opened guanosine nucleotides and thus, the number of detectable labels that will be chemically bonded to a polynucleotide in accordance with the invention. This provides a means to tailor the degree of labeling to particular applications. Notably, in the case of DMS-mediated guanosine methylation in the G-specific reaction in the Maxam-Gilbert DNA sequencing procedure, the degree of methylation can be stringently controlled to provide methylation of only one G residue in 10, one in 100 or one in 1,000, inter alia, and the same holds true in the present invention.

$N^7$ purine alkylation generally, and $N^7$ guanine alkylation in particular, produces a positively charged intermediate. For instance, $N^7$-alkylguanosine derivatives have a positive charge on $N^7$. Moreover, the $N^7$ substituent strongly affects the lability of the $C8-N^9$ bond. The more electron-accepting the substituents the more labile the bond. Thus, alkylating agents of the invention can be selected to provide a rate of imidazole ring-opening suitable to a wide variety of reaction conditions, if desired. See, for instance, Kochetkov et al., ORGANIC CHEMISTRY OF NUCLEIC ACIDS, PART B, Chapter 7, Plenum Press 1972.

Preferably, hydroxide is employed to cleave the $N^7$-alkylated purine and results in an imidazole ring-opening reaction. Base mediated cleavage of $N^7$-alkylated guanine according to the invention normally cleaves the $C8-N^9$ bond, opening the purine imidazole ring, providing a ring-opened $N^7$-formyl-$N^7$-alkyl-substituted compound, and this cleavage will be used herein to illustrate the process.

An alkylation and base-mediated ring-opening reaction are described in Maxam et al., supra, inter alia. The invention in the present application, however, provides for chemically bonding detectable labels, inter alia, to N-formyl groups of the ring-opened compounds and differs greatly from the subsequent steps of the procedure employed in the Maxam-Gilbert sequencing technique. The object in the sequencing technique is controlled lysis of the phosphodiester backbone of DNA, whereas in the present invention the backbone remains intact. Accordingly, in the Maxam-Gilbert procedure, base-mediated cleavage of the purine imidazole ring and strand scission by an elimination reaction that severs a phosphodiester bond are catalyzed with piperidine. In the present invention, conditions that would lead to strand scission are avoided. Instead, following base-mediated imidazole ring-opening, the N-formyl substituent is coupled to a detectable label, a functionalized linker, or a blocking or protecting group.

A wide variety of reactions by means of which a covalent bond is formed between a formyl group and another substituent are useful in the present invention for forming a covalent bond between the N-formyl group of a ring-opened purine and a desired addition substituent.

In a general sense, these reagents may serve three functions, providing (1) a reactive group for bonding to the formyl group of an $N^7$-formyl-$N^7$-alkylpurine, (2) a linking moiety, and (3) a second substituent which may be another reactive substituent, a blocking group which will generally later be removed to generate a reactive group for further derivatization, or a detectable label. It will be appreciated, however, that one, two or all three of these functions may be served by a single chemical entity.

Reactive substituents for forming a chemical bond with the $N^7$-formyl substituent of an $N^7$-formyl-$N^7$-alkylpurine include any substituents capable of forming a bond with the $N^7$-formyl group. Generally, the substituents will be those that do not deleteriously modify the alkylpurine as a result of the process of bond formation. A deleterious modification in this context will be understood to mean a modification that interferes with the particular application for which the modified alkylpurine is being prepared. Thus, reagents useful for bonding to the $N^7$-formyl group include those useful in the Wittig reaction, those useful in the aldol condensation, amines, hydrazides, semicarbazides, inter alia. Particularly useful reactive substituents for bonding to the $N^7$-formyl group are amines, hydrazides, semicarbazides.

Reactive groups useful in the invention include but are not limited to any that form the following linkages with the carbon atom of the N-formyl group, $=NNHCH_2R$, $=NNHCOR$, $=NHCH_2R$, $-NHR$, $=CHCOR$, $=CRR'$, $-OCH(R)R'$, wherein R and R' simply indicate other portions of the compounds which may ultimately be chemically bonded to the formyl group through the indicated linkages. It will be understood that R and R' in this context include the full range of substituents useful as linking and blocking group, as well as those useful as detectable labels, as set forth elsewhere herein in greater detail.

Preferred groups will be those bearing primary amine or hydrazine functions. Amines form Schiff bases with the formyl group, which can be stabilized by reduction to secondary amines, e.g. with $NaBH_3CN$. Hydrazines condense with formyl groups to form relatively stable hydrazones, which normally do not require further stabilization. The amine or hydrazone functions can be part of linkers that are previously or subsequently reacted with other moieties, eventually including the desired detectable label.

The linking group, when it is present in the reagent usually will be a linear or branched carbon chain which may also comprise N or S or both, and generally will comprise at least four atoms. It will be appreciated that the exact chemical composition of a linking group will be dictated by the particular application. Thus, the linking group will be stable to the reactions required for bonding to the $N^7$-formyl group, and also to other reactions that may be necessary to a given application, such as removing a blocking group, attaching a detectable label or the like.

Preferred linking groups include, but are not limited to the monomer, dimer or trimer of ε-amino caproic acid ($H_2N$-

($CH_2)_5$-COOH), and alkane diamines including 1,4-diaminobutane, 1,5-diaminopentane and 1,6-diaminohexane, inter alia. Particularly preferred among the ε-amino caproic acids and similar chains are those which are soluble in aqueous buffers.

Following formation of the ring-opened purine, the reaction conditions are adjusted to accommodate the formation of a bond between the N-formyl group and the reactive moiety of the substituent. Generally, the conditions will be such as not to unfavorably modify the nucleotide substrate in any way. Additional blocking groups, detectable labels and the like that can be used in accordance with the invention are set forth below.

The present invention also relates to compounds of the following formula, which may be conveniently produced by the methods of the present invention.

wherein,

A is —H or —OH;

B is —H, —OH, mono-, di- or triphosphate or a derivative thereof, or a blocking group for chemical polynucleotide synthesis, or it is a phosphodiester bond or a derivative thereof;

D is —H, —OH, mono-, di- or triphosphate or a derivative thereof, or a blocking group for chemical polynucleotide synthesis, or it is a phosphodiester bond or a derivative thereof;

E is an alkyl group;

F is a bond or linking moiety, and;

G is a detectable label or a blocking group.

Compounds of the invention therefore include but are not limited to ribo and deoxyribonucleosides and their derivatives, including DNA and RNA, wherein A is —H or —OH, respectively. Also within the scope of the invention are compounds of the above formula which comprise derivatives of —OH compatible with methods for synthesizing RNA.

Compounds of the invention include those wherein B is —H or —OH, or a mono-, di- or triphosphate or a derivative thereof. Included, among others, are RNA and DNA polynucleotides, wherein B will be a phosphodiester or a derivative of a phosphodiester; nucleosides and derivatives thereof, including nucleoside 3' monophosphates, nucleoside 3' diphosphates, and nucleoside 3' triphosphates; dideoxynucleosides and derivatives thereof.

Also included are compounds wherein B is a blocking (or protecting) group suitable for chemically synthesizing DNA or RNA. (The terms blocking group and protecting group are used interchangeably herein to refer to chemical groups that render a reactive substituent in a compound inert to a chemical process and allow the substituent or a derivative thereof subsequently to be regenerated. Such groups are well known in the art and are crucial to chemical methods of oligonucleotide and peptide synthesis, for instance.)

A variety of such 3' blocking groups for oligonucleotide synthesis are known to the art, as, for instance, described in Gait, M. J., OLIGONUCLEOTIDE SYNTHESIS, A PRACTICAL APPROACH, (IRL Press, 1984) which is herein incorporated by reference. One preferred blocking group of this type is the β-cyanoethyl N,N-diisopropyl phosphoramidite blocking group, which is extensively employed in substrates for automated oligonucleotide synthesis.

Compounds of the invention include those wherein D is —H or —OH, or a mono-, di- or triphosphate or a derivative thereof, or a phosphodiester bond. Included are RNA and DNA polynucleotides, wherein B will be a phosphodiester or a derivative of a phosphodiester; nucleosides and derivatives thereof, including nucleoside 5' monophosphates, nucleoside 5' diphosphates, and nucleoside 5' triphosphates; dideoxynucleosides and derivatives thereof, including especially dideoxynucleoside triphosphates, among others.

Also included are compounds wherein D is a blocking group suitable for chemically synthesizing DNA or RNA. A variety of 5' blocking groups for oligonucleotide synthesis are described in Gait, M. J., OLIGONUCLEOTIDE SYNTHESIS, A PRACTICAL APPROACH, (IRL Press, 1984). A preferred blocking group of this type is the dimethoxytrityl blocking group extensively employed in substrates for automated oligonucleotide synthesis.

In compounds of the invention illustrated by the above formula, E is an alkyl group, which may be a straight-chain, branched-chain, or cyclic alkyl, including alkyl substituted straight-chain, branched-chain, or cyclic alkyl groups. Preferably E will be a primary alkyl, especially a lower alkyl group. Highly preferred alkyl groups include methyl, ethyl, or benzyl alkyl groups, of which the methyl group is very highly preferred.

F is a covalent bonding function formed between the $N^7$-formyl group of $N^7$-formyl-$N^7$-alkylpurine and G. Most preferably, F comprises either —CH=N— or —$CH_2$N—.

F may be a direct bond formed by an $N^7$-formyl group and a substituent of a detectable label or it may be one or more linking groups for attaching at some distance a detectable label to the $N^7$-formyl group, or it may be an intermediate group, such as blocking group, capable of further derivatization to chemically bond a detectable label.

Accordingly, F may be a single substituent or it may be a more complex substituent. For instance, F may be any C-, N- or S- containing group that can serve as a linker group. Preferably, if F is a linking group, it will be a linear or branched carbon chain which may also comprise N or S or both, comprising at least four atoms.

When F comprises a linking group, it will usually have been derived from a divalent compound, that is a compound that contained two reactive groups, one that coupled to the $N^7$-formyl group and the other to couple to a second linking group, a blocking group or to a detectable label.

A variety of homobifunctional and heterobifunctional linking reagents known in the art are useful in the present invention. These reagents provide a reactive substituent for forming a bond with the formyl group of a ring-opened $N^7$-formyl-$N^7$-alkylpurine of the invention and a reactive substituent for forming a bond to a detectable label, or to another linking group or to a blocking agent.

Preferred linkers include the monomer, dimer or trimer of ε-amino caproic acid ($H_2N$—($CH_2)_5$—COOH), and alkane diamines including 1,4-diaminobutane, 1,5-diaminopentane and 1,6-diaminohexane, inter alia. Particularly preferred among the ε-amino caproic acids and similar compounds are those which are soluble in aqueous buffers.

Reactive substituents comprised by F for forming a chemical bond with the $N^7$-formyl substituent of an $N^7$-formyl-$N^7$-alkylpurine include any substituents capable of forming a bond with the $N^7$-formyl group. Generally, the substituents will be those that do not deleteriously modify the alkylpurine as a result of the process of bond formation. A deleterious modification in this context will be understood to mean a modification that interferes with the particular application for which the modified alkylpurine is being prepared. Thus, reagents useful for bonding to the $N^7$-formyl group include those useful in the Wittig reaction, those useful in the aldol condensation, amines, hydrazides, semicarbazides, inter alia. Particularly useful reactive substituents for bonding to the $N^7$-formyl group are amines, hydrazides, semicarbazides.

Reactive groups useful in the invention include but are not limited to any that form the following linkages with the carbon atom of the N-formyl group, =NNHCH$_2$R, =NNHCOR, =NHCH$_2$R, —NHR, =CHCOR, =CRR', —OCH(R)R', wherein R and R' simply indicate other portions of the compounds which may ultimately be chemically bonded to the formyl group through the indicated linkages. It will be understood that R and R' in this context include the full range of substituents useful as linking and blocking group, as well as those useful as detectable labels, as set forth elsewhere herein in greater detail.

Preferred groups will be those bearing primary amine or hydrazine functions. Amines form Schiff bases with the formyl group, which can be stabilized by reduction to secondary amines, e.g. with NaBH$_3$CN. Hydrazines condense with formyl groups to form relatively stable hydrazones, which normally do not require further stabilization. The amine or hydrazone functions can be part of linkers that are previously or subsequently reacted with other moieties, eventually including the desired detectable label.

Compounds according to the invention may include a detectable label, G. G may be any chemical group which has a physical or chemical characteristic which can be detected, and any label that can be detected by a physical or chemical method may be used in the invention.

Detectable labels of the invention may be determined by colorimetry, spectrophotometry, fluorimetry, methods for detecting radioactivity, and other methods well-known to the art.

Detectable labels of the invention include labels characterized by color, luminescence, fluorescence, radioactivity, ligand recognition, affinity binding, chemical reactivity and enzymatic activity, among others.

Included among the affinity binding labels are ligands of all types, lectin binding moieties, substrates and substrate analogs, co-factors, antigens, immunologically reactive substances and substituents such as epitopes, determinants and haptens and the like, and substances that comprise epitopes, determinants and haptens and the like, that bind antibodies, antibody derivatives, single chain antibodies and the like.

Included among the fluorescent compounds are 7-amino-4-methylcoumarin-3-acetyl hydrazide, fluorescein, rhodamine; among the lectin ligands are lactose, N-acetylglucosamine, N-acetylgalactosamine or mannose; among the antigen or antigen epitopes is dinitrophenyl; among the enzyme substrates are NADH and NADPH; and among the enzymes are horseradish peroxidase and alkaline phosphatase.

Other detectable labels useful in the invention, to mention just a few, include fluorescein isothiocyanates, dinitrophenylisothiocyanates, fluorodinitrobenzene, N-hydroxysuccinimidylbiotin, N-hydroxysuccinimidyl, dinitrobenzoate, aminobutyl ethyl isoluminol isothiocyanate, active esters of carboxyfluorescein, rhodamine, biotin adducts, dioxetanes, dioxamides, carboxyacridines, and carbohydrates.

Preferred detectable labels of the invention include biotin and digoxigenin. Preferred methods of detecting biotin and digoxigenin include enzyme immunoassays [EIAs] that employ alkaline phosphatase conjugated to avidin or to streptavidin, or to an antibody specific for digoxigenin.

Applications of the invention include all of the uses for bases, nucleosides, nucleotides, oligonucleotides and polynucleotides, particularly those containing labels. For instance, the present invention is a useful tool in recombinant DNA and other protocols involving nucleic acid hybridization techniques.

More specifically, oligonucleotides and nucleic acids containing a compound of the invention can be used as hybridization probes, capable of recognizing and specifically binding to complementary nucleic acid sequences, providing thereby a means of detecting, identifying, locating and measuring complementary nucleic acid sequences in a biological sample.

Biological samples include, among a great many others, blood or blood serum, lymph, ascites fluid, urine, microorganism or tissue culture medium, cell extracts, or the like, derived from a biological source, or a solution containing chemically synthesized protein, or an extract or solution prepared from such fluid from a biological source. It is further intended to include cells, tissue and other organic matter such as feces, food and plants.

Molecular probes containing a compound of the invention have a variety of applications. They can be used to detect and identify viral, fungal, bacterial and parasitic nucleic acid sequences, serving thereby to aid the diagnosis of various related human, animal and plant diseases. They can be similarly used for both diagnostic and quality control purposes to detect and identify viral, fungal and bacterial contaminants in foods and for DNA typing in forensic and paternity investigations.

Molecular probes containing the invention also can be used to identify nucleotide sequences to which proteins bind specifically. For instance, probes immobilized on solid supports can isolate and purify proteins which bind to sequences within the probes. Probes labeled with biotin, for example, can be bound to affinity chromatography supports, or magnetic beads bearing covalently coupled streptavidin. Proteins which bind to such biotin-labeled probes can be separated from a biological sample containing a variety of other proteins. Other methods for purifying proteins using a solid support are well known to the skilled artisan.

An oligonucleotide containing a modified nucleotide of the invention can be used as a primer to initiate nucleic acid synthesis at locations in a DNA or RNA molecule comprising the sequence complementary to the oligonucleotide sequence. The synthesized nucleic acid strand would have incorporated, at its 5' terminus, the oligonucleotide primer bearing the invention and would, therefore, be detectable by exploitation of the characteristics of the detectable label. Two such primers, specific for different nucleotide sequences on complementary strands of dsDNA, can be used in the polymerase chain reaction (PCR) to synthesize and amplify the amount of a nucleotide sequence. The detectable label present on the primers will facilitate the identification of desired PCR products. PCR, combined with techniques for preparing complementary DNA (cDNA) can be used to amplify various RNAs, with oligonucleotide primers again serving both to provide points for initiation of synthesis in the cDNA duplex flanking the desired sequence and to identify the desired product. Primers labeled with the invention may also be utilized for enzymatic nucleic acid sequencing by the dideoxy chain-termination technique.

Because the invention is derived by chemical incorporation of detectable labels into guanine or $N^7$-alkylguanine residues in a nucleic acid, the invention can be applied as a guanine-specific or 7-alkylguanine-specific adduct to measure or quantitate the amount of DNA present in a sample. For instance, the concentration of nucleic acid can be measured by comparing detectable labels incorporated into the unknown nucleic acid with the concentration of detectable labels incorporated into known amounts of nucleic acid.

Such a comparative assessment can be done using biotin where the respective concentrations are determined by an enzyme-linked assay utilizing the streptavidin-alkaline phosphatase conjugate and a substrate yielding a soluble chromogenic or chemiluminescent signal.

The present invention is further described by reference to the following illustrative examples.

EXAMPLE 1: Reduction using sodium borohydride of substituents in DNA formed by ring-methylation followed by base treatment.

These experiments show that the aldehyde group generated by scission of the C8-$N^9$ bond in 7-methyl guanine is reducible and could be used for incorporating a detectable label into DNA.

DNA was methylated by treatment with DMS in a neutral buffer for 10, 20 or 30 minutes, resulting in the formation in the DNA of successively increasing amounts of $N^7$-methylguanine. The methylated DNA was then treated with either sodium hydroxide or with sodium hydroxide and sodium borohydride, breaking the C8-$N^9$ bond in the methylated guanine nucleotides and generating either ring-opened $N^7$-formyl-$N^7$-methylguanine nucleotides or reduced ring-opened $N^7$-formyl-$N^7$-methylguanine nucleotides.

Figure 1:
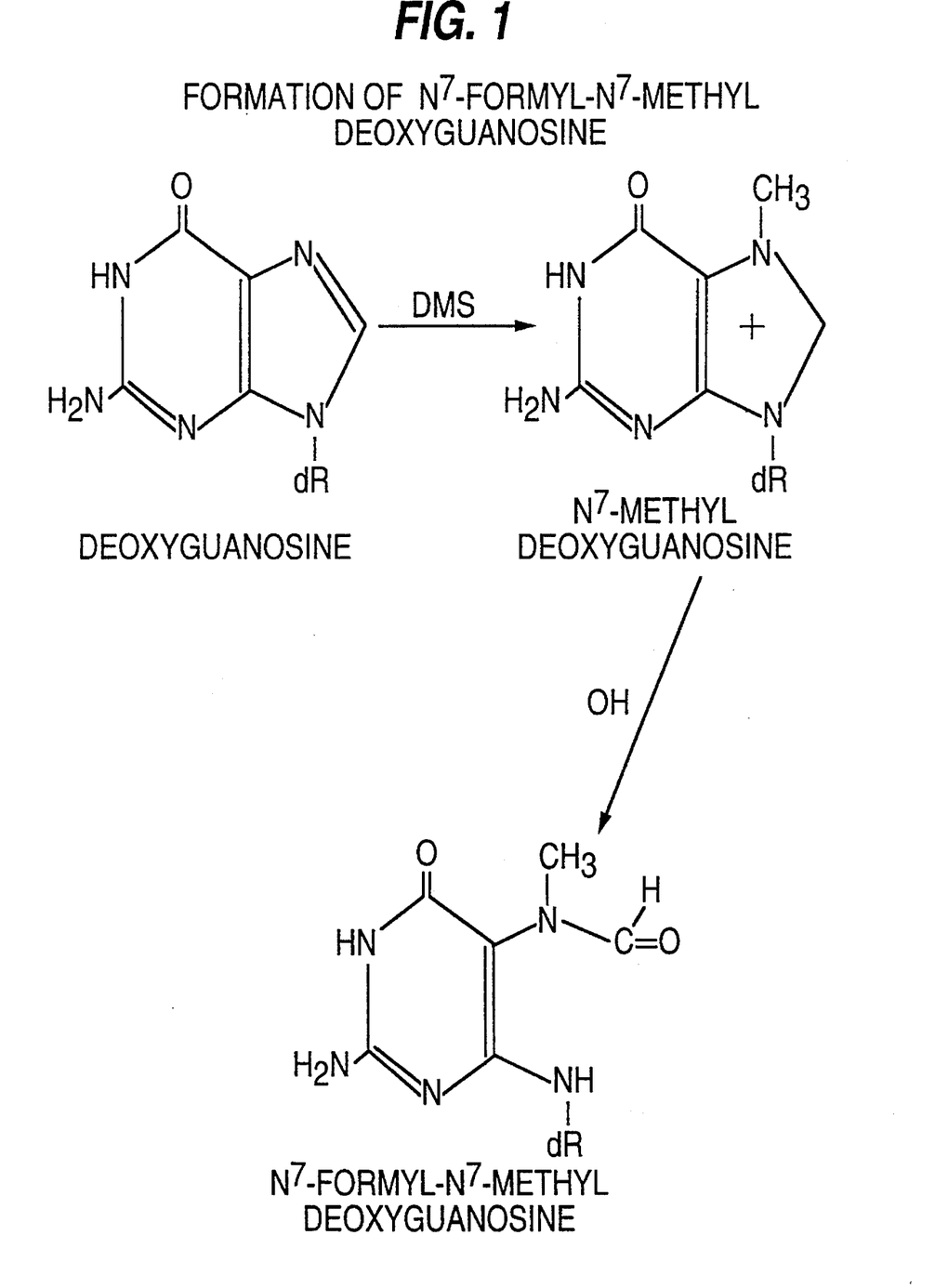
FIG. 1 is a diagram showing the formation of $N^7$-methyl-$N^7$-formyldeoxyguanosine by treating deoxyguanosine with dimethylsulfate (DMS) to form $N^7$-methyldeoxyguanosine, and then with base (OH) to open the alkylated purine ring to form ring-opened $N^7$-formyl-$N^7$-methyldeoxyguanosine.
Figure 2:
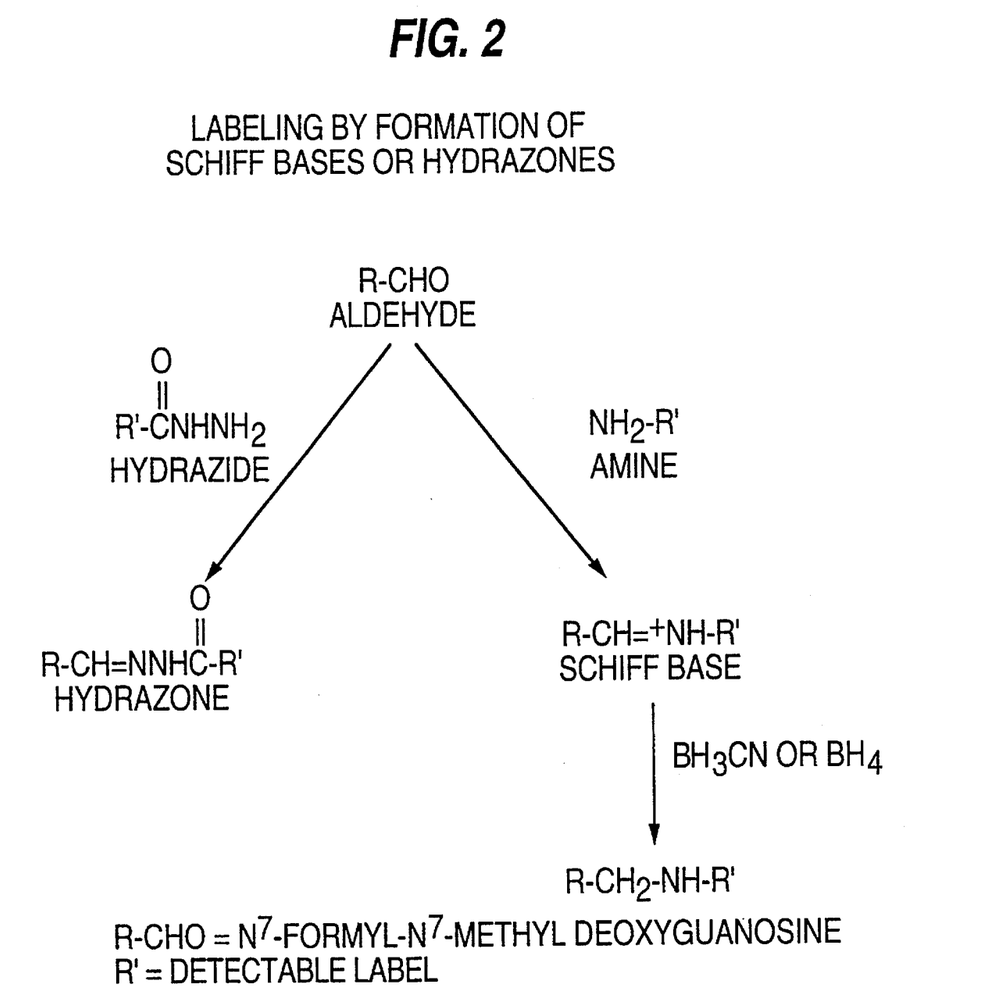
FIG. 2 is a diagram showing two reaction schemes for chemically bonding a detectable label ("detectable label" R') to a formyl substituent (aldehyde) in, inter alia, ring-opened $N^7$-formyl-$N^7$-methyldeoxyguanosine. In the reaction pathway on the left side of the diagram, a hydrazide of a detectable label is employed to form a hydrazone upon reacting with the formyl substituent. In the reaction pathway on the right side of the diagram, an amine of a detectable label is employed to form a Schiff base with the formyl group, which is then reduced with cyanoborohydride or $BH_4^-$.
Figure 3:
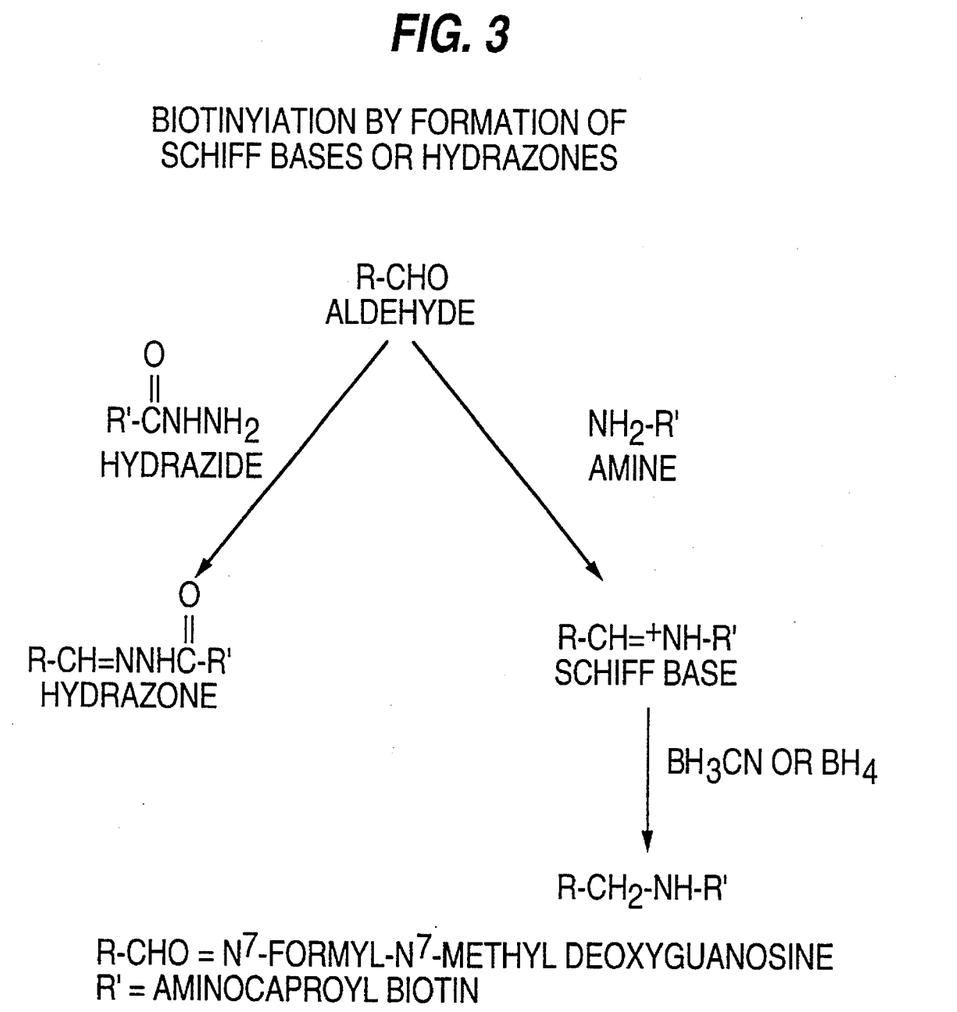
FIG. 3 is a diagram showing two reaction schemes for biotinylating the $N^7$-formyl substituent in ring-opened $N^7$-formyl-$N^7$-methyldeoxyguanosine. In the reaction pathway on the left side of the diagram, the hydrazide of aminocaproyl biotin is employed to form biotin aminocaproyl hydrazone upon reacting with the formyl substituent. In the reaction pathway on the right side of the diagram, diaminocaproyl biotin is employed to form a Schiff base upon reacting with the formyl group, which is then reduced with cyanoborohydride or $BH_4^-$.
Figure 4:
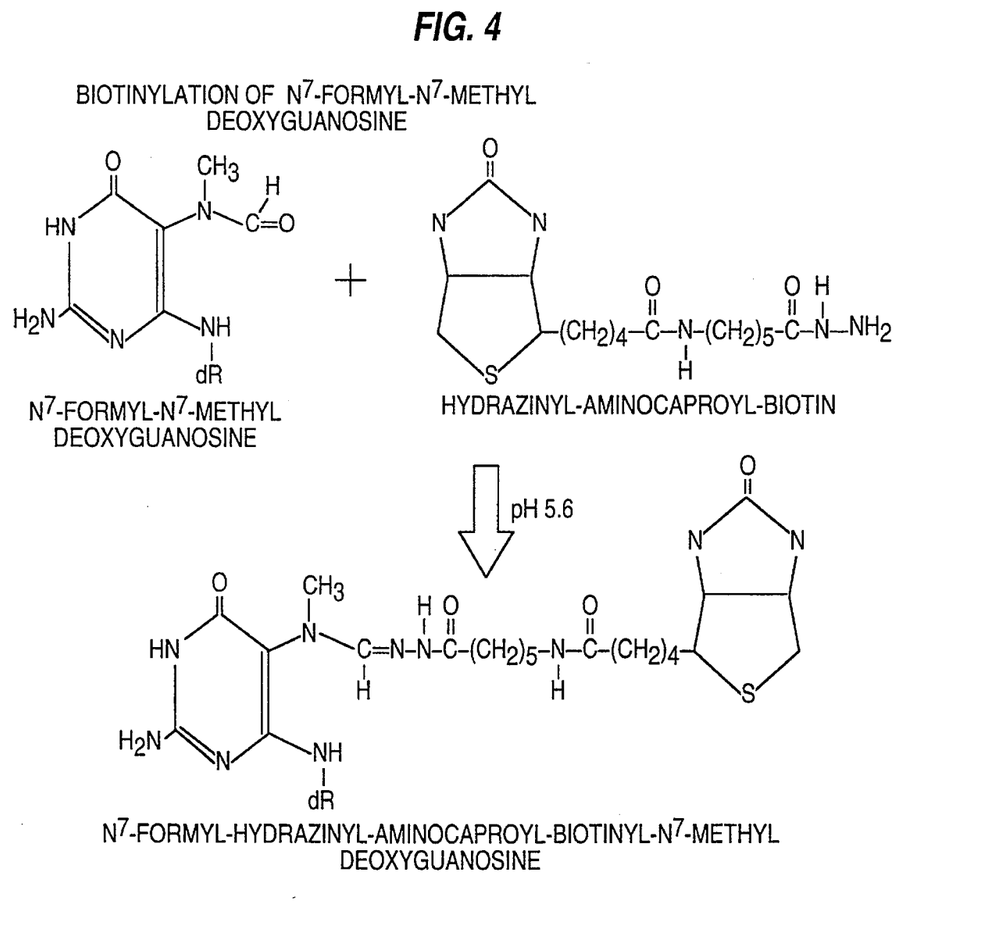
FIG. 4 is a more detailed diagram showing the formation of a biotin aminocaproyl hydrazone derivative of ring-opened $N^7$-formyl-$N^7$-methyldeoxyguanosine by reacting biotin aminocaproyl hydrazide with the formyl substituent of ring-opened $N^7$-formyl-$N^7$-methyldeoxyguanosine.
Figure 5:
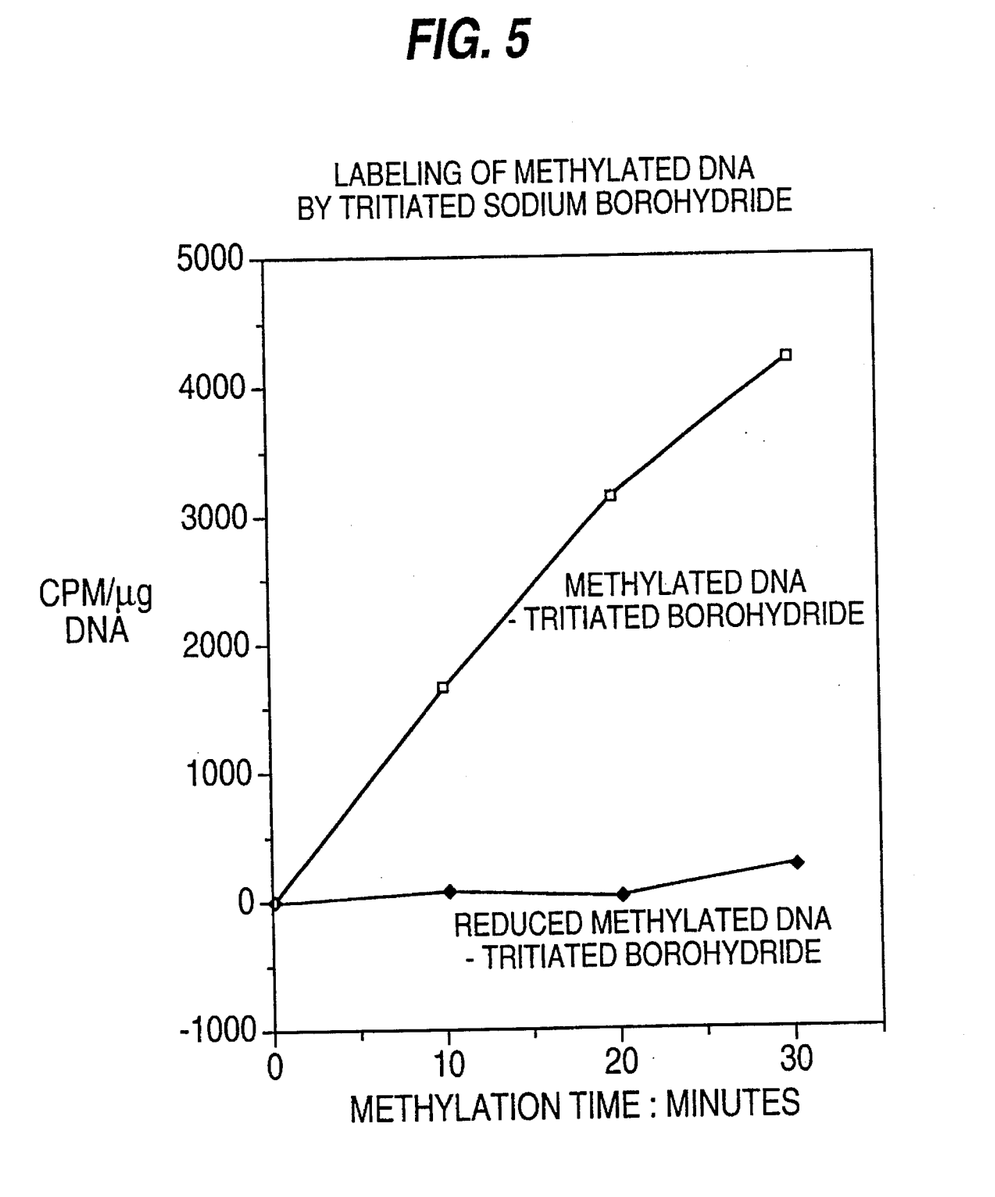
FIG. 5 is a graph showing that untreated DNA remains unlabeled in the presence of tritiated borohydride, but DNA treated in accordance with the invention incorporates tritium from the tritiating reagent in direct proportion to the extent of reaction with DMS.

The DNAs thus treated were then exposed to tritium-labeled sodium borohydride. As shown in FIG. 5, DNA which had not been reduced with unlabeled sodium borohydride took up tritium label and the extent of tritium uptake was directly proportional to the extent of methylation.

These experiments show clearly the generation of the reducible [formyl] group by alkylation and base treatment.

EXAMPLE 2: Biotinylation of bacteriophage λ DNA, and use of the biotinylated λ DNA to probe a Southern blot.

By means of the procedure set forth below, ring-opened $N^7$-formyl-$N^7$-methyl guanine residues were formed in λ DNA by treatment with DMS and sodium hydroxide. Biotin was attached to the carbon 8 aldehyde of the $N^7$-formyl-$N^7$-methyl guanine residues in the λ DNA by reaction with biotin-aminocaproyl hydrazide. The biotinylated λ DNA was hybridized to a Southern blot of λ DNA digested with HindIII, and detected by EIA using a streptavidin-alkaline phosphatase conjugate. Similar experiments were carried out using the biotinylated λ DNA to probe slot-blots of λ DNA. In addition, a sandwich assay was carried out in which biotinylated λ DNA was captured by avidin immobilized in microtiter plate wells and then measured by ELISA.

(1) Components of the Reaction:
 1. Bacteriophage Lambda DNA (λ DNA) (20 micrograms/50 microliters; Gibco-BRL; #5250SA) Chilled to 0° C.
 2. Buffered dimethylsulfate (DMS), consisting of 5 microliters of dimethylsulfate (Eastman Kodak) per milliliter 0.5M Sodium cacodylate, pH 8.0 containing 0.0001M EDTA. Chilled to 0° C.
 3. 0.4N NaOH.
 4. Sodium Acetate Buffer (4.0M Sodium Acetate, pH 5.6)
 5. Buffered biotin aminocaproyl hydrazide, consisting of 1 mg of biotin aminocaproyl hydrazide per milliliter of sodium acetate buffer.
 6. Spin columns containing a 0.9×4 cm bed of BioGel P2 (400 mesh).

(2) Reaction Protocol
 (a) Methylation and Ring Opening
 The methylation reaction was started by mixing 200 microliters of buffered DMS with 20 micrograms (50 microliters) of λ DNA and transferring the mixture to a 25° C. water bath. The mixture was incubated overnight (16 hours). 50 microliters of 0.4N NaOH were added and the mixture was incubated at 37° C. for 2 hours to generate aldehyde groups.

(b) Coupling of Biotin Hydrazide to DNA.
 50 microliters of 4M sodium acetate buffer were mixed with the methylated λ DNA to give a pH of 5.6 and 200 microliters of buffered biotin-aminocaproyl-hydrazide were added. The mixture was incubated overnight at 37° C. Biotinylated λ DNA was separated from unreacted biotin-aminocaproyl-hydrazide by centrifugation through a BioGel P2 spin column. Recovery of DNA was 85% (17 micrograms) in the column effluent.

(3) Results
As a test for the presence of biotin in the λ DNA probe, 300 ng of biotinylated λ DNA per milliliter was hybridized to a Southern blot of HindIII fragments of λ DNA (Example 5). The biotinylated λ DNA probe detected the 6.6 Kb HindIII fragment of λ DNA at an apparent concentration of 0.9 pg against a moderate background. Hybridization to slot-blots of serially diluted HindIII fragments of λ DNA detected 100 fg of target DNA, while biotinylated λ DNA captured by immobilized avidin in microtiter plates was detected at 0.6 pg per well.

EXAMPLE 3: Biotinylation of a synthetic oligodeoxynucleotide.

The present invention is further illustrated by the biotinylation of a synthetic oligodeoxynucleotide. 10 μg of a 48-mer oligodeoxynucleotide corresponding to the degenerate nucleotide sequence encoding the first 16 amino acids of the amino terminus of Streptococcus sobrinus glucan-binding protein (gbp1) is diluted in 50 μl of deionized water. All subsequent reactions are carried out as described above in EXAMPLE 2, using the synthetic oligonucleotide in place of λ DNA. Assaying the reaction products by electrophoresis in 20% polyacrylamide gels, Southern blotting the oligonucleotides onto a membrane, and detecting biotinylated species in the blot with streptavidin-alkaline phosphatase conjugate showed the presence of biotin in the oligonucleotides.

EXAMPLE 4: Biotinylation of transfer RNA.

RNA can be biotinylated using methods of the invention set forth hereinabove, and detailed procedures similar to those set forth in EXAMPLE 2.

For labeling RNA, deionized water for use in preparing buffers and other solutions is autoclaved and treated with 200 μl diethylpyrocarbonate per liter of water to inhibit the enzyme RNase. Where possible, buffers also are autoclaved. RNase-free, sterile plasticware is used in all labeling procedures.

5 μl of buffered DMS are thoroughly mixed with 195 μl of 0.5M cacodylate, 0.01M EDTA, pH 8.0 and 50 μl (500 ng) of tRNA in a 1.5 ml microcentrifuge tube. The mixture is incubated at 25° C., in a water bath, overnight Following the 25° C. incubation, sufficient 0.4N NaOH is added to the reaction mixture to achieve a pH of 10.0. The reaction mixture is then incubated at 25° C. for 1 hour to open the imidazole rings of $N^7$-methylguanosine residues formed in the tRNA as a result of the incubation with DMS.

The reaction is stopped by addition of 50 μl of 4.0M sodium acetate buffer to adjust the reaction mixture to pH 5.6.

Biotinylation of the ring-opened $N^7$-formyl-$N^7$-methylguanosine residues in the tRNA is carried out using biotin aminocaproyl hydrazide in the same manner as described in EXAMPLE 2 for λ DNA. Separation of the biotin-labeled tRNA from excess biotin aminocaproyl hydrazide also is accomplished as described for biotinylation of λ DNA in Example 2, using a gel permeation spin column. Biotin-RNA prepared in this manner may be used immediately or stored frozen at −20° C.

The presence of biotin in tRNA (and in other RNA's prepared in this way) is detected and quantitated by EIA analysis of dot or slot blots of serial dilutions of the biotinylated RNA diluted in 10 mM Tris-HCl, 1 mM EDTA, pH 8.0. The total amount of RNA is estimated by ethidium bromide fluorescence, while the amount of biotin incorporation is estimated in the colorimetric ELISA by comparison with a standard preparation of biotinylated RNA.

EXAMPLE 5: DNA titration using biotinylated λ DNA as a hybridization probe.

Bacteriophage λ DNA was biotinylated as described in EXAMPLE 2. Unlabeled λ DNA digested with HindIII was resolved into its fragments by electrophoresis in a 1% agarose gel. The HindIII digested λ DNA was applied to the gel lanes in amounts of 150 ng (lane 1), 10 ng (lane 2), 1 ng (lane 3), 500 pg (lane 5), 50 pg (lane 7), 10 pg (lane 9) and 1 pg (lane 11).

After electrophoresis the DNA was Southern blotted onto Nytran nylon membranes and hybridized to biotinylated λ DNA following procedures described in Selden, "Analysis of DNA Sequences by Blotting and Hybridization," Unit 2.9, pages 2.9.1–2.9.10 in Ausubel et al., CURRENT PROTOCOLS IN MOLECULAR BIOLOGY (John Wiley & Sons 1991).

After blotting and before hybridization the membranes were prehybridized at 42° C. for 6 hours. Denatured biotinylated λ DNA was diluted to 300 ng/ml in hybridization buffer and incubated with the membranes until hybridization was complete. The hybridized membranes were then washed and blocked by 30 minutes incubation in 3% BSA in PBS at room temperature. Blocked membranes were incubated 30 minutes at room temperature in streptavidin-alkaline phosphatase (SAAP) conjugate diluted 1:12,000 in PBS and then washed 4 times (10 minutes per wash) in PBS.

Bound SAAP was detected by incubation of membranes in 0.165 mg/ml 5-bromo-4-chloro-3-indolyl phosphate ("BCIP") and 0.33 mg/ml nitro blue tetrazolium ("NBT") in 0.1M Tris pH 9.6, 50 mM $MgCl_2$, 100 mM NaCl. The smallest amount of HindIII λ DNA detected by this chromogenic stain was 0.9 pg, in band 4 (6.6 Kbp) of lane 9.

Additional sensitivity was obtained using a chemiluminescent substrate. Blots containing 100 fg in lane 11 were treated as above, except that they were developed using a chemiluminescent substrate for alkaline phosphatase, in this case "LUMIPHOS 530" (Lumigen, Inc.). By these means 49 fg (band 1 in lane 11) of λ DNA was detected, against a heavy background, approximately 20-fold better than with the chromogenic substrates.

EXAMPLE 6: Detection of the E. coli lac z gene by hybridization with biotinylated phage M13mp19 DNA.

Single-stranded M13mp19 DNA, which contains one copy of the alpha fragment of the lac Z gene, was biotinylated as described for whole λ DNA in EXAMPLE 2, and used to probe E. coli genomic DNA in a slot-blot for the presence of the endogenous E. coli lac Z gene.

Thus, genomic DNA of E. coli strain Y1090 ("Y1090 DNA") was serial-diluted, in 10-fold steps, in 1X SSC, providing concentrations of genomic DNA ranging from 100 ng/100 μl to 1 pg/100 μl. The dilutions of Y1090 DNA were applied to Nytran membranes, 100 μl per slot, using a slot-blot apparatus (Life Technologies Inc., Bethesda Research Laboratories).

Slot-blot membranes were then baked 1 hour at 80° C., prehybridized and hybridized as described in EXAMPLE 5. Biotinylated M13mp19 was diluted to 300 ng/ml in the hybridization solution. The slot-blot was incubated in 5 ml of hybridization solution at 42° C. overnight. Processing of the probe slot-blots, through incubation with SAAP and development with the NBT/BCIP substrate were as described in EXAMPLE 5.

The lac Z gene was detected in slots containing 100 pg to 1 μg of E. coli Y1090 genomic DNA. Detection of lac Z in 100 pg genomic DNA represents visualization of about 75 fg of lac Z gene, since a single copy of the $3.51 \times 10^3$ bp lac Z gene is present in the E. coli genome, which contains $4.7 \times 10^6$ bp, i.e., $(3.5 \times 10^3/4.7 \times 10^6)(100 \times 10^{-12}) = 7.45 \times 10^{-14}$.

EXAMPLE 7: Use of biotinylated oligonucleotide as a hybridization probe for Southern blots of restricted genomic DNA.

The gbp1 oligonucleotide biotinylated in EXAMPLE 3 serves as a hybridization probe to detect the gbp1 gene in a Southern blot of EcoRI restricted Streptococcus sobrinus 6715-49 genomic DNA. Streptococcal genomic DNA is digested to completion with EcoRI, then 10 μg aliquots are resolved in multiple lanes by electrophoresis overnight in a 1% agarose gel in 1 X Tris-Acetate-EDTA buffer ("TAE," 20 X TAE buffer contains 242 g Tris base, 7.1 ml glacial acetic acid, 37.2 g EDTA at pH 8.5). A control lane contains 10 μg of E. coli Y1090 genomic DNA digested to completion with EcoRI.

The Southern blot is prepared, prehybridized and hybridized by the procedures described in EXAMPLE 5. The biotinylated gbp1 oligonucleotide hybridization probe is diluted to a final concentration of 300 ng/ml in hybridization buffer. After hybridization overnight at 42° C. in 5 ml per filter of hybridization solution, excess probe is washed away and the annealed biotinylated gbp1 oligonucleotide probe is visualized as described in EXAMPLE 5. A single band of target DNA, of approximately 8 kbp, is detected in all lanes containing S. sobrinus DNA but not in the E. coli Y1090 DNA control lane. This result replicates a similar experiment utilizing this oligonucleotide, 5'-end labeled with $^{32}P$, as a hybridization probe.

EXAMPLE 8: $T_m$ of biotinylated λ DNA.

λDNA was biotinylated in the manner described in EXAMPLE 2. Melting temperatures ($T_m$) were determined for biotinylated λ DNA and unmodified λ DNA. Each DNA was dissolved at 15 µl/ml in 1X SSC buffer (150 mM NaCl, 15 mM sodium citrate, pH 7.0). DNA absorbance was monitored at 260 nm while increasing the temperature in increments of 5° C., from room temperature to 100° C. The $T_m$ of biotinylated λDNA was 84° C., while that of unmodified λDNA was 89° C.

EXAMPLE 9: Biotinylation of dGTP and end-labeling DNA using the biotinyl-dGTP and terminal deoxynucleotidyl transferase.

Deoxyguanosine triphosphate (dGTP), dissolved at 1 mg/ml in cacodylate buffer is biotinylated as described in EXAMPLE 2, with the omission of spin-column chromatography. The biotin-labeled dGTP ("Bio-dGTP") is separated from unbound biotin aminocaproyl hydrazide by reverse-phase chromatography on a C18 column, with a 0 to 80% gradient of acetonitrile ($CH_3CN$). Bio-dGTP is freed from acetonitrile in a rotary evaporator under vacuum at 37° C. then redissolved in deionized water.

To biotinylate the *S. sobrinus* gbp1 48-mer oligonucleotide using terminal deoxynucleotidyl transferase (TdT), the reaction mixture contains:

100 mM sodium cacodylate, pH 7.0
1 mM $CoCl_2$
0.1 mM dithiothreitol
4 pmoles oligonucleotide (as 3' termini)
20 µm Bio-dGTP
2.5 µg bovine serum albumin
10 International Units terminal deoxynucleotidyl transferase The reaction is incubated at 37° C. for 30 minutes and terminated by adding 2 µl of 0.5M EDTA. End-labeled oligonucleotide is separated from unincorporated Bio-dGTP by centrifugation through a BioGel P2 spin column. If desired, TdT is removed by phenol extraction and the oligonucleotide is precipitated from the aqueous phase by the addition of two volumes of absolute ethanol and incubation at −70° C. for at least 1 hour. The use of $CoCl_2$ allows end-labeling of ribonucleotides as well as deoxyribonucleotides.

EXAMPLE 10: A competitive enzyme linked assay for DNA.

Microtiter plate wells ("IMMULON 2" microtiter plates from Dynatech Laboratories, Inc.) were coated by overnight incubation at room temperature with 300 µl/well of 5 g/ml avidin in PBS (Pierce Chemical Company), and then blocked 30 minutes with 300 µl/well of 0.1M $NH_4Cl$. The reporter enzyme for the assay was biotinylated alkaline phosphatase ("BAP"; Pierce Chemical Company) diluted from a 1 mg/ml PBS stock solution. Useful dilutions of BAP for the detection of nanogram quantities of DNA ranged from 1/40,000 through 1/100,000, while detection of picogram levels of DNA was optimum at BAP dilutions of 1/100,000 through 1/140,000 (see insets in FIGS. 6 and 7).

*E. coli* Y1090 genomic DNA was biotinylated by the procedure of EXAMPLE 2. Biotinylated DNA was diluted in PBS to provide two dilution series: 1 to 100 ng of biotinylated DNA per 200 µl and 1 to 100 pg of biotinylated DNA per 200 µl. 200 µl aliquots of each biotinylated DNA dilution series, or of PBS only, were incubated in avidin-coated wells for two hours at room temperature on a rotary shaker. Following three washes with PBS, the wells received 200 µl aliquots of BAP at appropriate dilutions and incubation was continued, as above, for two more hours.

Plates were washed six times with PBS and then 200 µl aliquots of p-nitrophenylphosphate (4 mg/ml 10% diethanolamine, 0.5 mM $MgCl_2$, pH 9.8) were added to each well. Rates of the ensuing enzyme reactions were determined in a kinetic platereader (Easy Reader EA 400 AT; SLT Labinstruments) at 405 nm. End-point optical density values at 405 nm were determined after 1 hour incubation at room temperature.

Figure 6:
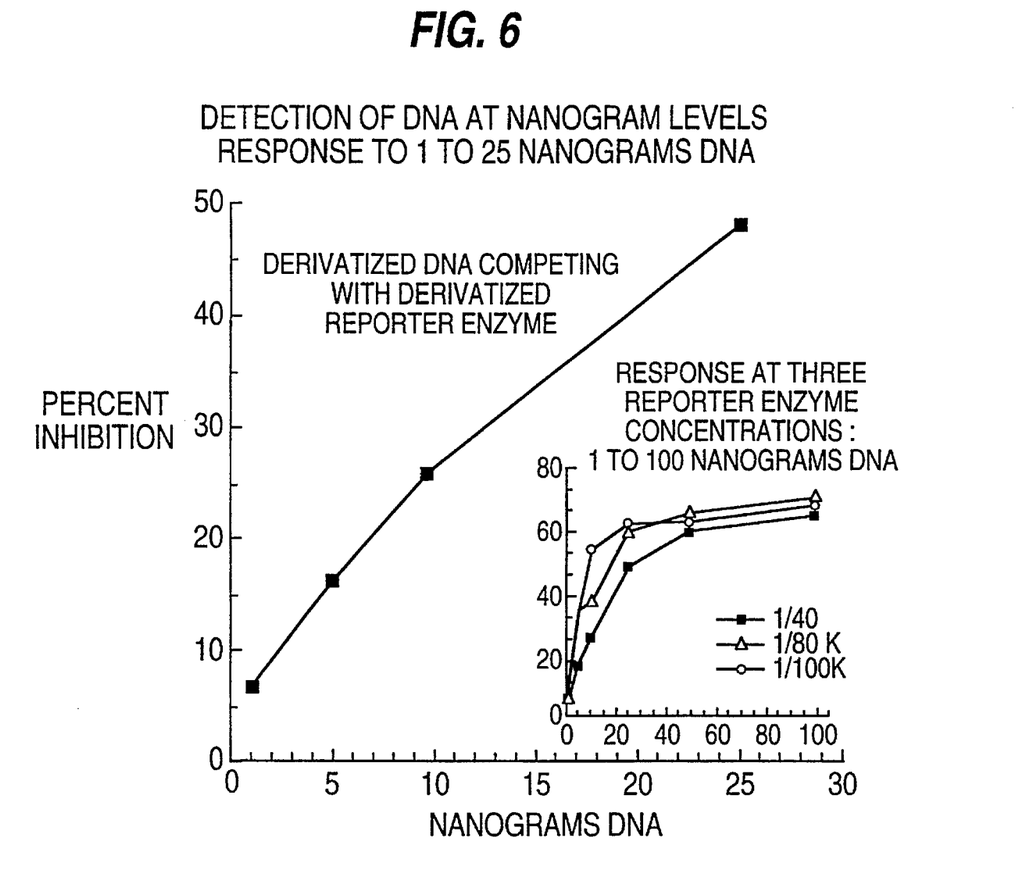
FIG. 6 is a graph showing that a competitive enzyme assay according to the invention provides a linear and sensitive measure of DNA in a sample containing 1 to 25 nanograms of DNA. The assay was carried out by measuring the ability of DNA biotinylated in accordance with the invention to inhibit binding of a biotin enzyme conjugate to immobilized avidin.
Figure 7:
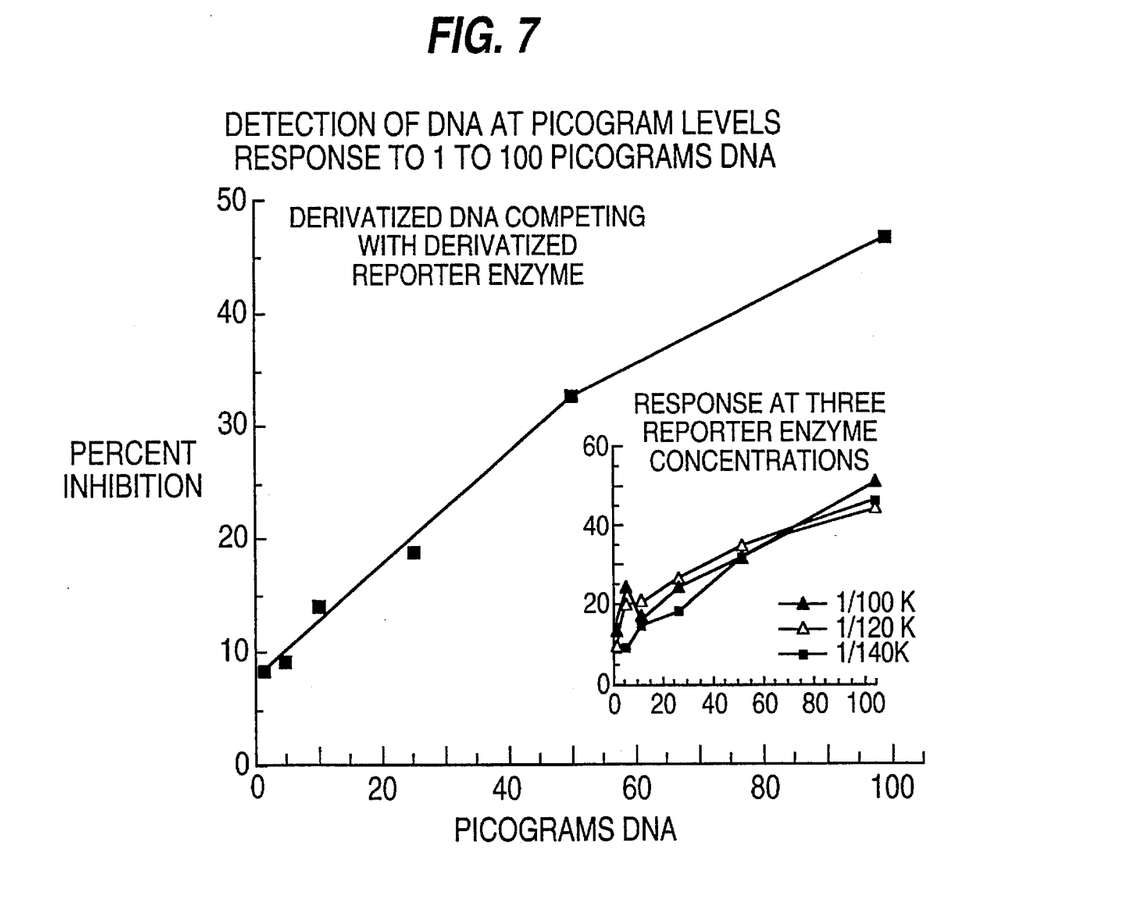
FIG. 7 is a graph showing that a competitive enzyme assay of the invention provides a linear and sensitive measure of DNA in a sample in a range of 1 to 100 picograms of DNA. The assay was carried out as described in FIG. 6.

FIGS. 6 and 7 show values of percent inhibition for the nanogram and picogram ranges, respectively. Insets in these figures compare responses at various reporter enzyme dilutions. These competitive assays are capable of measuring DNA over concentration ranges of 1 to 25 ng/200 µl (FIG. 6) and 1 to 100 pg/200 µl (FIG. 7).

What is claimed is:

1. A method for detecting in a sample a purine base-containing polynucleotide analyte, comprising the steps of:
   (a) hybridizing to said polynucleotide analyte a detectably-labeled, imidazole ring-opened $N^7$-alkyl-$N^7$-formyl purine contained within a polynucleotide probe capable of hybridizing to said polynucleotide analyte to form a complex; and,
   (b) detecting said polynucleotide analyte by detecting said label in said complex.

2. A competitive binding method for quantifying a polynucleotide analyte containing at least one purine nucleotide, comprising the steps of:
   (a) immobilizing on a solid support a first member of an affinity binding pair;
   (b) preparing a reporter enzyme by covalently coupling to said enzyme a second member of said affinity binding pair;
   (c) converting said purine of said polynucleotide analyte to an imidazole ring-opened $N^7$-alkyl-$N^7$-formyl derivative attached via said formyl group to a second member of said affinity pair either directly or through a linking moiety;
   (d) consecutively contacting said first member of said affinity binding pair with the products of steps (b) and (c), in any order, so that said polynucleotide analyte and said reporter enzyme compete for binding to said first member of said affinity pair immobilized on a solid support;
   (e) contacting bound or unbound reporter enzyme with a signal-producing substrate for said reporter enzyme;
   (f) quantifying said signal; and,
   (g) relating the amount of said signal to the amount of said polynucleotide analyte in said sample.

3. The method of claim 2, wherein said first member of said affinity binding pair is avidin or streptavidin and said second member of said affinity binding pair is biotin.

4. An enzyme-linked immunoassay method for the quantification of a polynucleotide analyte containing at least one purine nucleotide, comprising the steps of:
   (a) producing an imidazole ring $N^7$-alkylated purine nucleotide in said polynucleotide;
   (b) cleaving the $C^8$-$N^9$-bond in said imidazole ring of said $N^7$-alkylated purine with a base to produce an $N^7$-alkyl-$N^7$-formyl purine derivative of said analyte polynucleotide, wherein the imidazole ring of said purine is open between $C^8$ and $N^7$;

(c) adding to the product of step (b) an anti-purine derivative antibody and a reporter DNA, wherein said reporter DNA comprises a standard DNA containing an imidazole ring-opened-$N^7$-alkyl purine linked to biotin through the $N^7$ ($C^8$)-formyl group of said ring-opened purine so as to form an antibody-analyte polynucleotide-DNA complex;

(d) capturing said complex on a second antibody-coated solid support;

(e) determining the amount of said reporter DNA in said complex with a signal-generating enzyme covalently bound to avidin or streptavidin;

(f) relating said amount of reporter DNA in said complex to the amount of analyte polynucleotide.

5. A process for labeling a polynucleotide containing at least one purine nucleotide, comprising the steps of:

(a) reacting the $N^7$ imidazole ring nitrogen of said purine nucleotide with an alkylating reagent to form an $N^7$-alkylated purine nucleotide in said polynucleotide;

(b) reacting the $C^8$-$N^9$ bond of said imidazole ring in said $N^7$-alkylated purine nucleotide in said polynucleotide with a base so as to form an $N^7$-alkyl-$N^7$-formyl nucleotide, wherein said imidazole ring of said purine is opened between $C^8$ and $N^7$;

(c) covalently attaching a detectable label to said $N^7$-formyl group; and, (d) isolating the resulting detectably labeled imidazole ring-opened $N^7$-alkyl-$N^7$-formyl purine nucleotide-containing polynucleotide product.

6. A process of claim 5, wherein said alkylating agent is dimethylsulfate or diethylsulfate.

7. A process of claim 5, wherein said nucleophilic agent is an alkali base.

8. A process of claim 5, wherein said detectable label is attached to said formyl group by a process comprising the step of reacting an amino group-containing reagent with said $N^7$-formyl group under conditions such that a Schiff base forms between an amino group of said reagent and said $N^7$-formyl group, wherein said Schiff base-forming reagent is a detectable label or a moiety for covalently bonding a detectable label to said $N^7$-formyl group, either directly or through a linking group.

9. A process of claim 5, wherein said detectable label attached to said formyl group is selected from the group consisting of a radionuclide, chromagen, fluorogen, chemilumogen, an affinity moiety, an enzyme and an immunoreactive moiety.

10. A process of claim 9, wherein said affinity moiety is biotin and said immunoreactive moiety is digoxigenin.

11. A kit for detecting in a sample a polynucleotide containing a purine nucleotide, comprising a $N^7$-methyl-$N^7$-formyl guanine nucleotide containing polynucleotide.

12. A kit according to claim 10, wherein said $N^7$-methyl-$N^7$-formyl guanine containing polynucleotide contains a detectable label attached at said formyl group.

13. A kit according to claim 12 wherein said detectable group is selected from the group consisting of a radionuclide, a chromogen, a fluorogen, a chemilumogen, a member of an affinity binding pair, an enzyme and an immunoreactive moiety.

14. A kit according to claim 13, wherein said member of an affinity binding pair is biotin.

15. A kit according to claim 14, further comprising a solid support coated with avidin or streptavidin.

16. A kit according to claim 15, further comprising a biotinylated reporter enzyme.

17. A kit, comprising dimethylsulfate, sodium hydroxide and a detectable label for labeling the $N^7$-formyl group in $N^7$-methyl-$N^7$-formyl purine nucleotide.

18. A kit according to claim 16, wherein said enzyme is alkaline phosphatase.

19. A kit containing $N^7$-formyl-labeled $N^7$-methyl-$N^7$ formyl purine nucleotide.

* * * * *